United States Patent [19]
Esin et al.

[11] Patent Number: 5,269,188
[45] Date of Patent: Dec. 14, 1993

[54] CONTINUOUS SELF TEST TIME GATE ULTRASONIC SENSOR AND METHOD

[75] Inventors: Alexander J. Esin, Skokie; Boris S. Rosselson, Des Plaines, both of Ill.

[73] Assignee: Rosemount Inc., Eden Prairie, Minn.

[21] Appl. No.: 37,523

[22] Filed: Mar. 24, 1993

Related U.S. Application Data

[63] Continuation of Ser. No. 737,180, Jul. 29, 1991, abandoned.

[51] Int. Cl.⁵ .................... G01N 29/02; G01N 29/22
[52] U.S. Cl. ............................. 73/610; 73/10 V; 367/93
[58] Field of Search ............ 73/597, 599, 600, 602, 73/610, 614, 10 V, 290 V, 612; 367/93

[56] References Cited

U.S. PATENT DOCUMENTS

| | | | |
|---|---|---|---|
| 3,269,172 | 8/1966 | McGaughey | 73/614 |
| 4,131,872 | 12/1978 | Inoue et al. | 367/93 |
| 4,240,281 | 12/1980 | Lather et al. | 73/10 V |
| 4,299,114 | 11/1981 | Silvermetz et al. | 73/1 H |
| 4,316,183 | 2/1982 | Palmer et al. | 340/621 |
| 4,384,491 | 5/1983 | Brown et al. | 73/861.28 |
| 4,394,824 | 7/1983 | Kanda et al. | 73/610 |
| 4,446,735 | 5/1984 | Weilacher | 73/610 |
| 4,448,207 | 5/1984 | Parrish | 128/771 |
| 4,459,689 | 6/1984 | Biber | 367/93 |
| 4,470,299 | 9/1984 | Soltz | 73/290 |
| 4,480,474 | 11/1984 | Kazama et al. | 73/614 |
| 4,482,889 | 11/1984 | Tsuda et al. | 367/93 |
| 4,542,656 | 9/1985 | Johnson | 73/861.28 |
| 4,578,997 | 4/1986 | Soltz | 73/290 |
| 4,630,245 | 12/1986 | Dam | 367/93 |
| 4,655,084 | 4/1987 | Renzel | 73/600 |
| 4,676,098 | 6/1987 | Erienkämper et al. | 73/290 |
| 4,704,905 | 11/1987 | Arora | 73/602 |
| 4,708,022 | 11/1987 | Johnson | 73/861.28 |
| 4,708,191 | 11/1987 | Block et al. | 164/160 |
| 4,715,226 | 12/1987 | Dorr | 73/290 V |
| 4,735,097 | 4/1988 | Lynnworth | 73/861.28 |
| 4,765,186 | 8/1988 | Dieulesaint et al. | 73/290 |
| 4,770,038 | 9/1988 | Zuckerwar et al. | 734/290 V |
| 4,785,664 | 11/1988 | Reebs | 73/290 V |
| 4,787,240 | 11/1988 | McShane | 73/290 V |
| 4,787,407 | 11/1988 | Vogel | 137/2 |
| 4,815,323 | 3/1989 | Ellinger et al. | 73/290 |
| 4,821,569 | 4/1989 | Soltz | 73/290 |
| 4,833,918 | 5/1989 | Jean et al. | 73/290 |
| 4,868,797 | 9/1989 | Soltz | 367/98 |
| 4,896,535 | 1/1990 | Duckart et al. | 73/290 V |
| 4,909,080 | 3/1990 | Kikuta et al. | 73/290 V |
| 4,920,796 | 5/1990 | Duckart et al. | 73/290 V |
| 4,954,997 | 9/1990 | Dieulesaint et al. | 367/13 |
| 4,984,449 | 1/1991 | Caldwell et al. | 73/49.2 |
| 5,126,946 | 6/1992 | Ko | 73/599 |

OTHER PUBLICATIONS

Ultrasonic Testing, Edited by T. Szilard, 1982, pp. 463–467 and 488 (Section 12.3).

Primary Examiner—Hezron E. Williams
Assistant Examiner—Rose M. Finley
Attorney, Agent, or Firm—Westman, Chaplin & Kelly

[57] ABSTRACT

A time gate ultrasonic sensor measures a physical property of a material, such as the presence of the material, within a defined space. The sensor includes at least one transducer connected to a support structure and positioned generally adjacent the defined space for transmitting and receiving ultrasonic signals across the defined space. The ultrasonic signals include a main waveform which travels across the defined space and a self-test waveform which travels along the support structure. The sensor monitors the received ultrasonic signals during a main time window to sense whether the main waveform is present in the received signals. The sensor senses the physical property of the material within the defined space as a function of whether the main waveform is present within the time window. The sensor performs a self-test each measurement cycle by determining whether the self-test waveform is present during a self-test time window which is different from the main time window.

33 Claims, 5 Drawing Sheets

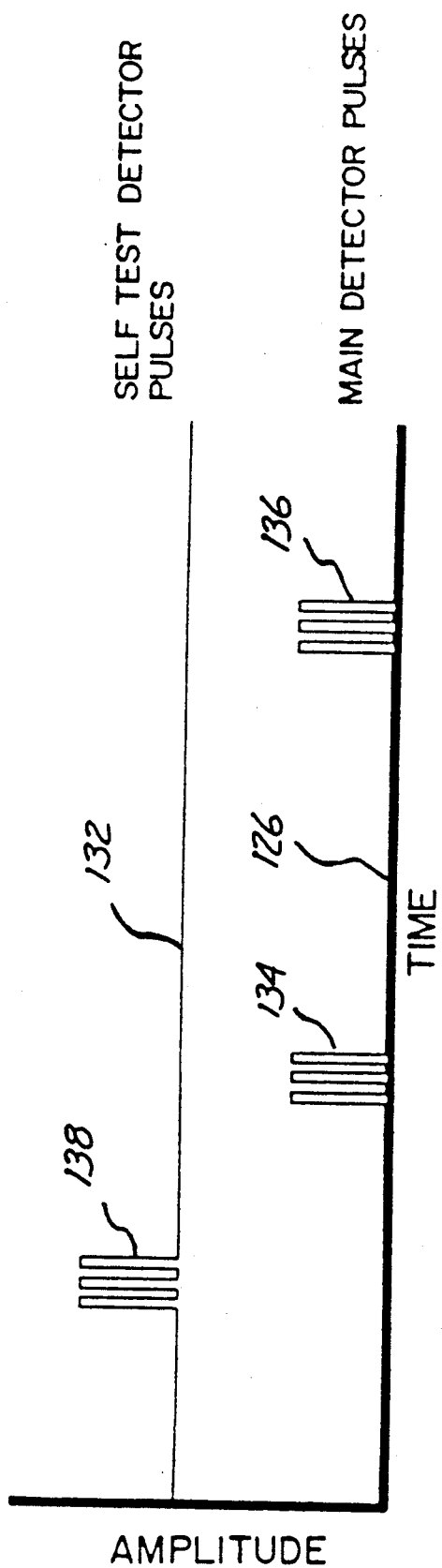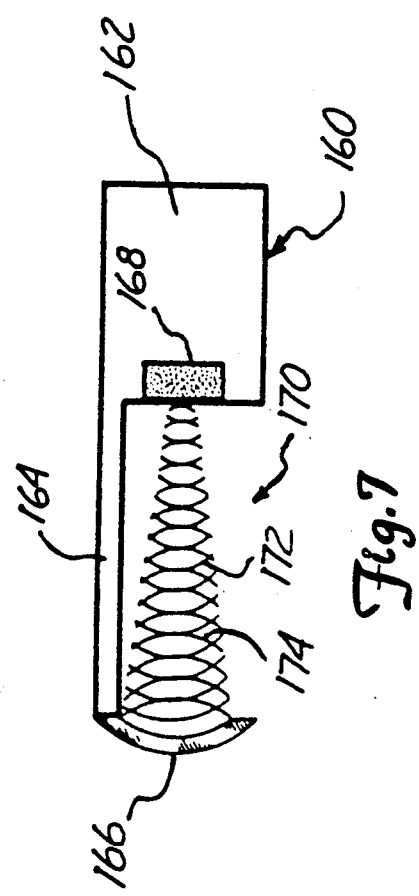

CONTINUOUS SELF TEST TIME GATE ULTRASONIC SENSOR AND METHOD

This is a continuation of application Ser. No. 07/737,180 filed on Jul. 29, 1991, abandoned as of the date of this application.

BACKGROUND OF THE INVENTION

The present invention relates to ultrasonic sensors for measuring a physical properties of materials within a defined space, and relates more particularly to a time gate ultrasonic sensor.

Various ultrasonic distance measuring and level measuring systems are known. For example, Ellinger et al. U.S. Pat. No. 4,815,323 teaches an "echo ranging" ultrasonic transducer transmitting an ultrasonic signal which is reflected from a liquid surface in an aircraft fuel container and then sensed. The round-trip time from sending to receiving is measured and the fuel quantity and density are computed in a central processing unit as a function of the round trip time and stored data.

In another type of ultrasonic sensor as taught by U.S. Pat. No. 4,299,114 to Silvermetz et al., an ultrasonic transmission between transmit and receive transducers closes a feedback loop of a circuit which oscillates when feedback increases to a predetermined amount. When a material level in a container rises to a level where the transmit and receive transducers are mounted, the higher amount of feedback through the material causes the circuit to oscillate. This type requires a relatively large difference between the amount of feedback with liquid and the amount of feedback with air for stable operation. Undesired feedback through a sensor body can reduce stability, as well. If air in entrapped in the material, feedback can be reduced and sensing fails. This type of sensor typically is quite large and not suitable for insertion in a container through a small hole such as a ¾" NPT threaded hole. In this type of sensor, misalignment of the transducers can reduce feedback through the materials so that sensing fails.

Ultrasonic sensors can include additional crystals (transducers) mounted or "piggybacked" on the sensing (receiving) crystals for a "self-test" function. The additional crystals are driven to excite the receiving crystal to complete the feedback loop to test the functioning of the receiving crystal without material in the gap. This does not completely test the ability of the- sensor to sense material in the gap, however, since it does not detect that a crystal has become un-bonded from the sensor body. This arrangement increases the overall size and complexity of the sensor and wiring, as well.

Silvermetz et al U.S. Pat. No. 4,299,114 discloses another self-test configuration in which, during test mode, an ultrasonic system monitors ultrasonic transmission through a support structure between a transmit crystal and a receive crystal. The crystals are connected in an oscillator feedback loop which oscillates if the system is operational. The system is deemed operational if the amplitude of the ultrasonic signals transmitted through the support structure is sufficient to maintain oscillation. However, this configuration is not easily adaptable to operate when the sensor includes a plastic support structure, because the attenuation in plastic weakens feedback and it is difficult to sustain oscillation.

SUMMARY OF THE INVENTION

The present invention relates to a time gate ultrasonic sensor which measures a physical property of a material within a defined space (gap) as a function of the velocity at which ultrasonic signals travel through the defined space. For example, the sensor can measure liquid level in a container by sensing the presence of the liquid within the defined space.

The ultrasonic sensor includes at least one transducer connected to a support structure and positioned generally adjacent the defined space for transmitting and receiving ultrasonic signals. The ultrasonic signals include a main waveform which travels across the defined space and a self-test waveform which travels along the support structure. The sensor monitors the received ultrasonic signals to sense whether the main waveform is present in the received signals during a main time window and whether the self-test waveform is present within a self-test time window. The sensor senses the physical property of the material within the defined space (which can be various solids, slurries, foams or other process materials) as a function of whether the main waveform is present within the main time window. The sensor senses the integrity of the sensor as a function of whether the self-test waveform is present within the self-test time window.

Ultrasonic signals generally travel faster in liquids than in gas (which can be air or a process gas) and faster in solids than in liquids. In one embodiment, the sensor measures liquid level by sensing the presence or absence of the liquid within the defined space. The presence of the main waveform within the main window is dependent upon whether the ultrasonic signals traveled through a liquid or a gas because of the different travel velocities. If the main waveform is present within the main time window, the ultrasonic signals traveled through a liquid. If the main waveform is not present within the main time window, the ultrasonic signals traveled through a gas because it takes much longer to receive the main waveform signal.

The sensor can measure material density and material level simultaneously because the time it takes the signal to travel through the material is related to the density of the material. In this embodiment the time windows can be adjusted to sense material density as well as the presence or absence of the material within the gap. The ultrasonic sensor can measure the interface between two materials in the gap if the density of the two materials is known.

In one embodiment, the ultrasonic sensor includes a transmit transducer and a receive transducer separated by the gap. The support structure includes a stem or stems between the transmit transducer and the receive transducer. In another embodiment, the support structure includes a vessel or pipe having walls with a circumference and an interior diameter which defines the gap. The transmit transducer and the receive transducer are connected to the vessel walls such that the ultrasonic signals travel from the transmit transducer to the receive transducer across the gap.

In yet another embodiment, the ultrasonic sensor includes a single transducer which both transmits and receives the ultrasonic signals. In this embodiment, the support structure includes an ultrasonic reflective surface positioned across the gap opposite the transducer such that the ultrasonic signals travel from the transducer, across the gap to the reflective surface, and then back to the transducer. The reflective surface can include a concave surface with a curvature selected to focus the reflected signal across the gap toward the transducer. In the embodiment in which the support structure includes a vessel or a pipe, the single transducer is connected to the vessel wall such that the ultrasonic signals travel from the transducer across the interior diameter to a surface on the wall opposite the transducer and reflect back to the transducer.

The time gate configuration of the present invention also provides an accurate and reliable method of testing the integrity of the ultrasonic sensor by using the self-test waveform which travels through the support structure. Since ultrasonic signals typically travel faster in solids than in liquids and air, the first waveform received is the self-test waveform which traveled along the support structure because it is a solid material. The second signal received is the main waveform which traveled across the gap. The self-test waveform should always be present with each transmitted signal.

The sensor monitors the received ultrasonic signals during a predetermined self-test time window to detect the presence of the self-test waveform within the self-test time window. The presence or absence of the self-test waveform is representative of sensor integrity. This method tests the functionality of each individual transducer and the ability of the transducers to detect a liquid across the gap. If a receive transducer becomes unbonded from the support structure, this failure would be detected because the self-test waveform would not pass through the support structure. A continuous self-test can be performed even with process material in the gap and without adding piggyback transducers to test the transmit and receive transducers individually. This reduces the complexity and size of the overall sensor.

BRIEF DESCRIPTION OF THE DRAWINGS

FIG. 6 is a graphical representation of main waveform detector pulses and self-test detector pulses which are present in the ultrasonic sensor circuit shown in FIG. 4.

FIG. 7 is a sectional view of a single crystal ultrasonic sensor in accordance with the present invention.

DETAILED DESCRIPTION OF THE PREFERRED EMBODIMENTS

The present invention is a time gate ultrasonic sensor which senses physical properties of material within a defined space by gating ultrasonic signals received at a receive crystal during specific times or "windows" when the sensor looks for a main waveform which traveled through a sensor gap and a self-test waveform which traveled through the sensor body. The presence or absence of the main waveform in the main window is indicative of the presence or absence of the material within the gap and the presence of the self-test waveform within the self-test time window is indicative of the functionality of the sensor.

Figure 1:
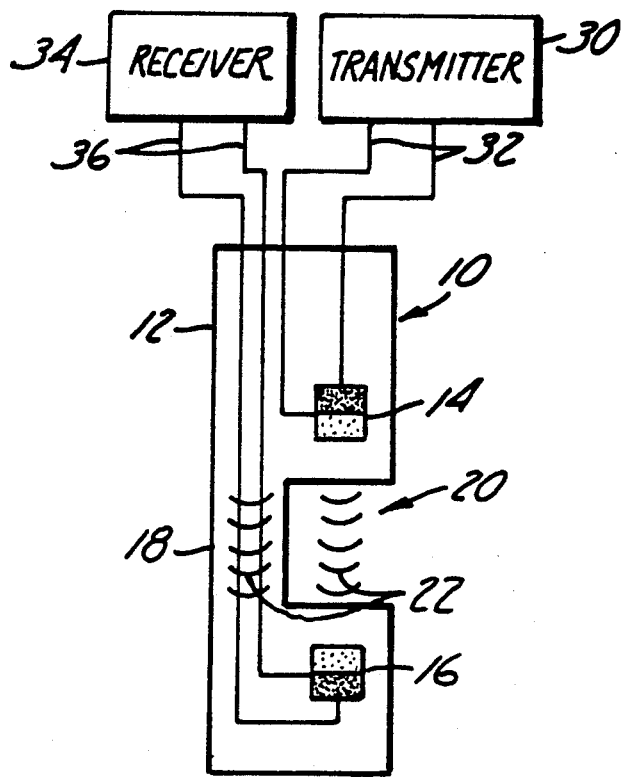
FIG. 1 is a sectional view of a time gate ultrasonic sensor in accordance with the present invention.

FIG. 1 is a sectional view of an ultrasonic sensor in accordance with the present invention. Sensor 10 includes a support structure 12, ultrasonic transmit transducer (crystal) 14 and ultrasonic receive transducer (crystal) 16. Support structure 12 includes stem 18 and gap 20. Stem 18 is also known as a bridge. Transducers 14 and 16 are mounted to support structure 12 such that they transmit and receive ultrasonic signals 22 across gap 20 and along stem 18. Support structure 12 can be constructed out of a variety of materials such as metal or plastic. In one typical construction transducers 14 and 16 are mounted in a pair of cavities in half-bodies of structure 12 which are secured to stem 18. Stem 18 is formed from a solid metal or plastic having a channel in which to route lead wires 36. The entire sensor 13 is then hermetically sealed.

Transmit transducer 14 is connected to transmitter 30 through electrical leads 32. Transmitter 30 periodically supplies electronic transmit pulses on leads 32 to transducer 14. When transmitter 30 delivers a transmit pulse to transmit transducer 14, the pulse energizes (or excites) transducer 14 causing the transducer to resonate at its natural frequency. Transducer 14 emanates ultrasonic signals 22 which travel through gap 20 and stem 18. The ultrasonic signals that travel through gap 20 are referred to as a main waveform, while the signals that travel through stem 18 are referred to as a self-test waveform.

Receive transducer 16 is connected to receiver 34 through electrical leads 36. Receive transducer 16 converts ultrasonic signals 22 into electrical signals which are applied to leads 36.

The absorption of ultrasonic signals 22 crossing gap 20 is inversely related to the density of the material in the gap. Therefore, when gap 20 is void of liquid the attenuation of the main waveform is significantly greater than when liquid is present in the gap. The absorption is particularly great at high frequencies such as above several kilohertz and higher. When gap 20 is empty, the signal which travelled through the gap is substantially a null signal. When gap 20 is filled with a liquid, the main waveform is received by transducer 16. The main waveform causes transducer 16 to resonate and generate electrical signals on leads 36. As a result, the presence or absence of the main waveform at receive transducer 16 is representative of the presence or absence of a liquid within gap 20.

The ultrasonic signals 22 that pass through stem 18 (the self-test waveform) should always be present with each transmitted pulse. This signal can be used for a self-test function. A continuous self-test can be performed regardless of whether material is present in gap 20. The self-test function will be discussed in greater detail below.

Sensor 10 can be used to measure physical properties of material within gap 20. For example, sensor 10 can measure liquid level in a vessel by sensing the presence or absence of liquid within gap 20. Sensor 10 can be secured to a flange mounted fitting, such as a standard NPT ¾" inch fitting. The fitting is then secured to a wall of a vessel containing material to be measured. As described in greater detail below, the sensor of the present invention can be constructed to fit within very small fittings to allow greater versatility in various applications.

The time gate technology of the present invention does not require that the transmit and receive transducers be connected by a conventional sensor "stem" as shown in FIG. 1. The two transducers can be constructed individually provided they are connected by some structure which conducts the self-test waveform. This allows them to be mounted on a pipe or vessel of any configuration constructed of any material with any wall thickness as long as the transmit and receive transducers are mounted pointing toward each other as shown in FIG. 2.

Figure 2:
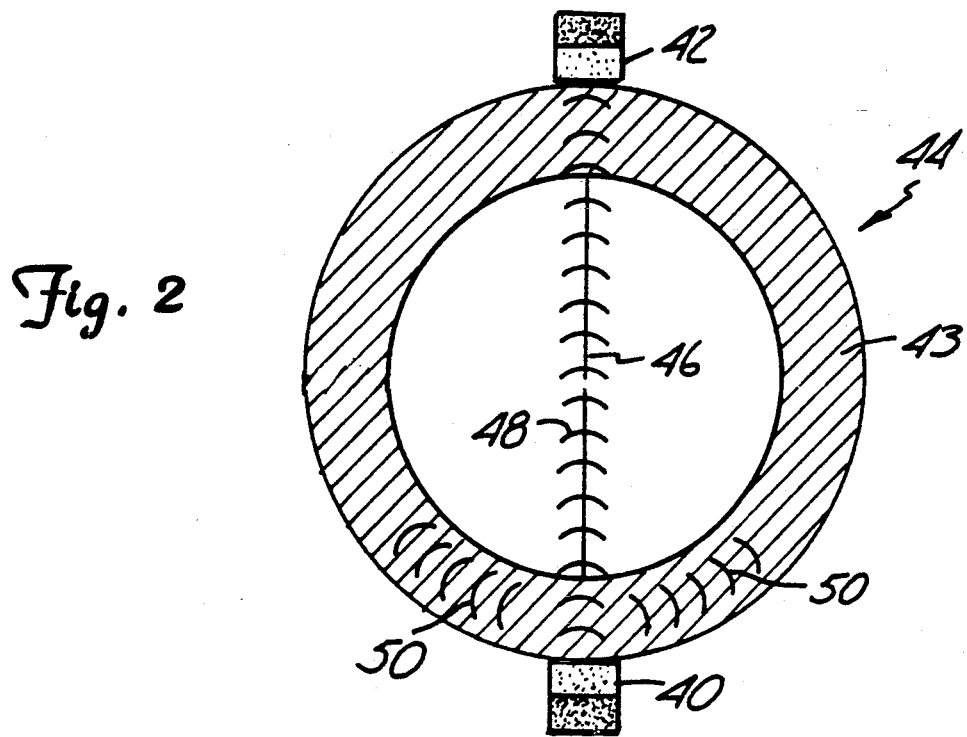
FIG. 2 is a sectional view of a time gate ultrasonic sensor attached to a pipe in accordance with the present invention.

FIG. 2 is a sectional view of an ultrasonic sensor attached to a pipe, in accordance with the present invention. Transmit transducer 40 and receive transducer 42 are mounted to wall 43 of pipe 44 such that the transducers face one another. Pipe 44 includes an interior diameter 46 which defines the "gap". Main waveform 48 travels from transmit transducer 40 toward receive transducer 42 along interior diameter 46. Self-test waveform 50 travels along the circumference of wall 43 from transmit transducer 40 to receive transducer 42. Wall 43 serves as a stem similar to stem 18 shown in FIG. 1. Wall 43 is therefore a substitute for stem 18.

Figure 3:
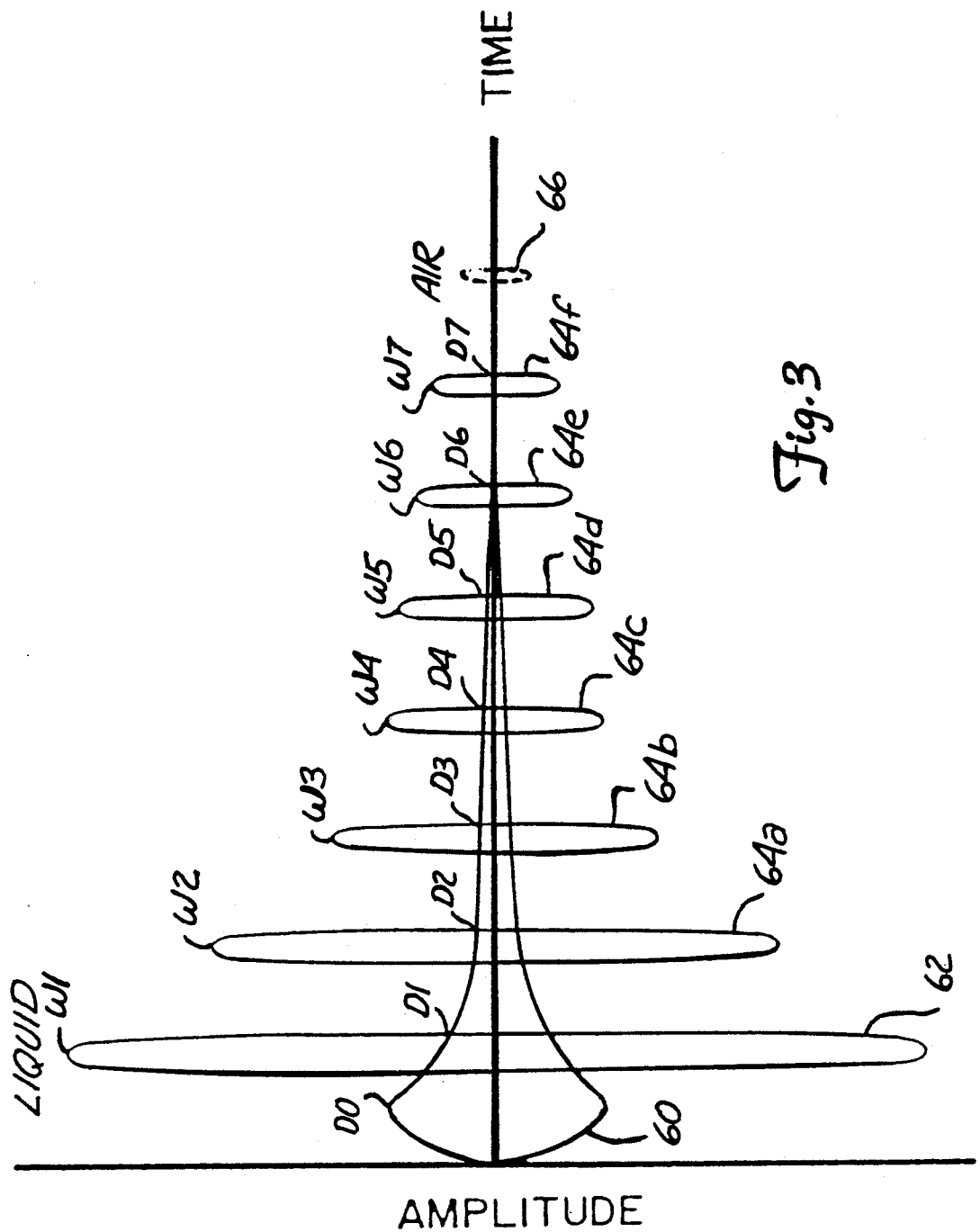
FIG. 3 is a graphical representation of a main waveform and a self-test waveform received by the ultrasonic sensors shown in FIGS. 1 and 2.

FIG. 3 is a graphical representation of the main waveform and the self-test waveform received by receive transducers 16 and 42 shown in FIGS. 1 and 2, respectively and illustrates the amplitude of the received ultrasonic signals as a function of time. Ultrasonic signals travel faster in liquids than in gas and faster in solids than in liquids. Therefore, the velocity at which ultrasonic signals 22 travel through gap 20 is a function of the presence or absence of liquid in the gap (i.e. liquid level). Since ultrasonic signals travel faster in solids than in liquids, the first signal received is self-test signal 60 which traveled through the stem (or supporting wall). The second signal received is main waveform 62 which traveled through the liquid in the gap. The amplitude of self-test signal 60 approaches zero following its peak amplitude DO when the signal first arrived. Main waveform 62 is followed by subsequent waveforms 64a-64f caused by multiple reflections across the gap. Waveform 66 shown in dotted lines represents a received signal which traveled through air (no liquid in the gap). Waveform 66 arrives significantly later with a significantly smaller amplitude than waveforms 62 and 64a-64f which travelled through a liquid.

In oscillator-type ultrasonic sensors used in the prior art, the transmit and receive transducers are connected in a feedback loop which is stable when the gap is void of process material. This is called a "dry" condition. When material enters the gap the circuit goes into oscillation. This is called a "wet" condition. A number of problems are inherent with the oscillator-type design that are not encountered with the present invention. First, the wet/dry signal ratio may not be large enough for stable operation. This can be caused by too much signal passing through the stem of the sensor body, or the attenuation of air being only slightly greater than the attenuation of the process material. Second, the consistency of the process material can affect the sensor performance. If the material has a high concentration of entrapped air the circuit may not oscillate.

In the present invention, when level is measured, the amplitude of the main signal is measured in the main time window, while the signal from the stem is separated in time (either before or after the main time window depending on the time delay through the stem) so that it does not present interference. Rather than being straight, the stem can have a "U" shape, a coil shape or other longer shape to provide a longer ultrasonic path to delay the self-test signal until after the main waveform. On the other hand, when density is measured, the parameter measured is time, not amplitude. Amplitude is not used to sustain oscillation as in the prior art. The equivalent of the "wet/dry" ratio is significantly and consistently higher. This greatly improves quality and reliability. The equivalent ratio, W1/D1, is the ratio of the amplitude W1 of the "wet" signal 62 that traveled through the process material in the gap to the amplitude D1 of the "dry" signal 60 that traveled through the sensor stem at the time the "wet" signal 62 is received. Since this time is significantly later than the initial arrival of signal 60 that traveled through the sensor stem, its amplitude D1 is significantly smaller than its peak amplitude DO. If the first signal received through the gap is too close to the peak amplitude D0, a later reflected signal can be used for a greater equivalent "wet/dry" ratio. The wet/dry ratio of an oscillator-type ultrasonic sensor is W1/D0 which is smaller than W1/D1.

Figure 4:
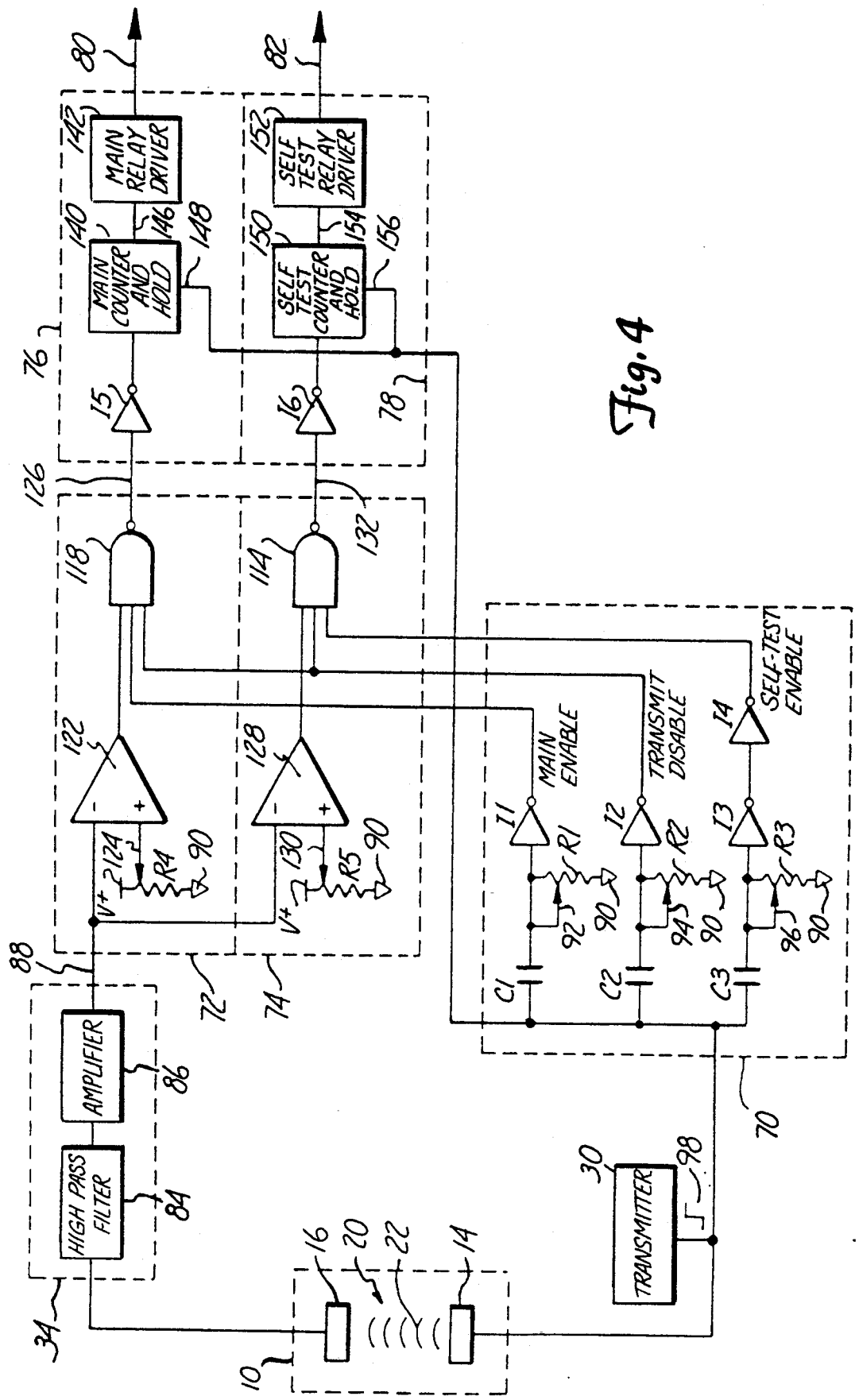
FIG. 4 is a schematic diagram of an ultrasonic sensor circuit in accordance with the present invention.

FIG. 4 is a schematic diagram of a time gate ultrasonic sensor circuit in accordance with the present invention. The circuit includes sensor 10, transmitter 30, receiver 34, time gate block 70, main waveform detector/comparator block 72, self-test waveform detector/comparator block 74, main waveform integrator block 76 and self-test waveform integrator block 78. Time gate block 70 generates enable signals which "gate" detector/comparator blocks 72 and 74 at certain times to open windows where integrator blocks 76 and 78 look for the main and self-test waveforms received by receiver 34. Integrator blocks 76 and 78 provide outputs 80 and 82 which are representative of the presence or absence of the main and self-test waveforms within their corresponding time windows. The presence or absence of the main waveform is representative of the presence or absence of a liquid within gap 20 of sensor 10. The presence or absence of the self-test waveform is representative of the integrity of sensor 10. The amplitude of the self-test waveform can be used to measure sensor degradation.

Sensor 10 includes transmit transducer 14 and receive transducer 16. Transmitter 30 is connected between transmit transducer 14 and time gate block 70. Transmitter 30 includes an oscillator circuit which operates with repetition rates typically from 10 Hz to 5 KHz. With the oscillator, transmitter 30 excites transmit transducer 14 with a 25 volt transmit pulse lasting between one-fourth and one-half of the transmit transducer's natural transmit period. The transmit pulse causes transmit transducer 14 to resonate and generate ultrasonic signals 22 which travel across gap 20 and stem 18 (shown in FIG. 1). The ultrasonic signals 22 are received by receive transducer 16. Receive transducer 16 applies electrical signals which are representative of ultrasonic signals 22 to high pass filter 84. High pass filter 84 applies a filtered signal to amplifier 86. The filtered signal is amplified on amplifier output 88.

The time gate windows are generated by time gate block 70 in response to a rising edge 98 (FIG. 4) of the transmit pulse generated by transmitter 30. Time gate block 70 includes capacitors C1, C2 and C3, resistors R1, R2 and R3, and inverters I1, I2, I3 and I4. Capacitor C1 is connected between transmitter 30 and inverter I1. Resistor R1 is connected between ground terminal 90 and the node between capacitor C1 and inverter I1.

Resistor R1 is a variable resistor having a center tap 92 which is connected to the node between capacitor C1 and inverter I1. Inverter I1 generates a main waveform enable signal at its output.

Capacitor C2 is connected between transmitter 30 and inverter I2. Resistor R2 is connected between ground terminal 90 and the node between capacitor C2 and inverter I2. Resistor R2 is a variable resistor having a center tap 94 which is connected to the node between capacitor C2 and inverter I2. Inverter I2 generates a transmit pulse disable signal at its output.

Capacitor C3 is connected between transmitter 30 and inverter I3. Resistor R3 is connected between ground terminal 90 and the node between capacitor C3 and inverter I3. Resistor R3 is a variable resistor having a center tab 96 which is connected to the node between capacitor C3 and inverter I3. Inverter I4 is connected to the output of inverter I3. Inverter I4 generates a self-test waveform enable signal at its output.

The rising edge 98 of each transmit pulse is integrated by three RC time constants within time gate generator 70. Capacitor C1 and resistor R1 form a first time constant which controls the length of time the main waveform enable signal is active (logic HIGH). Capacitor C2 and resistor R2 form a second time constant which controls the length of time the transmit pulse disable signal is active. Capacitor C3 and resistor R3 form a third time constant which controls the length of time the self-test waveform enable signal is active. These enable signals are illustrated in FIG. 5.

Figure 5:
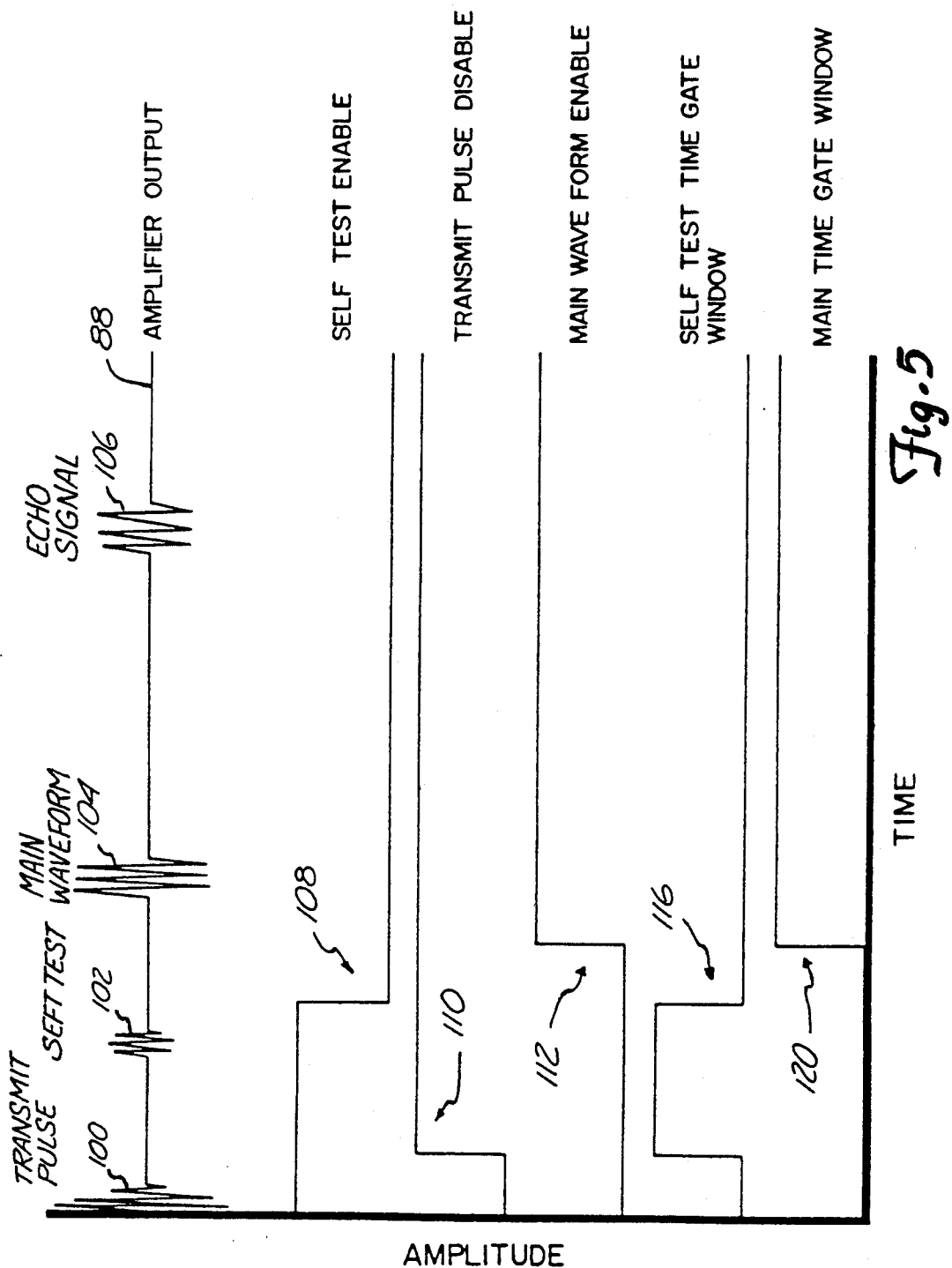
FIG. 5 is a graphical representation of various signals which are present in the ultrasonic sensor circuit shown in FIG. 4.

FIG. 5 is a timing diagram which provides a graphical representation of various signals within the time gate ultrasonic sensor shown in FIG. 1 which has a short stem during one cycle of transmitter 30. The graph represents signal amplitude as a function of time. Amplifier output 88 is shown at the top of the diagram. The first waveform to arrive is transmit pulse waveform 100. This waveform is generated by transmit transducer 14 when it begins to vibrate. The second waveform to arrive is self-test waveform 102 which traveled through sensor stem 18, because ultrasonic signals travel faster in solids than in liquids and in gases. The third waveform to arrive is main waveform 104 which traveled through a liquid in sensor gap 20. The fourth waveform to arrive is an echo signal of main waveform 104 caused by reflections in gap 20.

Waveform 108 illustrates the self-test waveform enable signal. When rising edge 98 (shown in FIG. 4) arrives at time gate generator block 70, the self-test waveform enable signal initially goes HIGH. After the third time constant, controlled by capacitor C3 and resistor R3, the self-test waveform enable signal goes LOW.

Waveform 110 illustrates the transmit pulse disable signal. The transmit pulse disable signal goes LOW at the rising edge 98 of the transmit pulse and remains LOW for the second time constant controlled by capacitor C2 and resistor R2. After the second time constant, the transmit pulse disable signal goes HIGH. The second time constant is selected to temporarily disable detector/comparator blocks 72 and 74 to prevent detection of transmit pulse waveform 100.

The transmit pulse disable signal 110 and the self-test waveform enable signal 108 are logically NANDed together at NAND gate 114 (FIG. 4) to create a self-test time gate window 116 (shown in FIG. 5). Self-test time gate window 116 is selected to enable self-test waveform detector/comparator 74 to detect the presence of self-test waveform 102 during self-test time gate window 116. The presence of self-test waveform 102 during self-test time gate window 116 is indicative of a functioning sensor. The absence of self-test waveform 102 during self-test time gate window 116 is indicative of a non functioning sensor.

Waveform 112 illustrates the main waveform enable signal. At the rising edge 98 of the transmit pulse, main waveform enable signal 112 goes LOW, and remains LOW for the first time constant controlled by capacitor C1 and resistor R1. After the first time constant, main waveform enable signal 112 goes HIGH. Main waveform enable signal 112 and transmit pulse disable signal 110 are logically NANDed together at NAND gate 118 (FIG. 4) to generate main waveform time gate window 120 (shown in FIG. 5). Main waveform time gate window 120 enables main waveform detector/comparator block 72 to detect the presence or absence of main waveform 104 only during the main waveform time gate window. If main waveform 104 is present within main waveform time gate window 120, the ultrasonic signals traveled through a liquid. If main waveform 104 is not present within main waveform time gate window 120, the ultrasonic signals travel through a gas, because it takes much longer to receive the main waveform signal. Further, main waveform 104 attenuates in air to such an extent that the signal received at receive transducer 16 is substantially a null signal. The main waveform time gate window 120 closes at the end of each cycle of transmitter 30. However, time gate generator block 70 can easily be modified to close the main waveform time gate window prior to the end of each cycle.

Main waveform detector/comparator block 72 is connected between amplifier 86 and main waveform integrator block 76. Block 72 includes resistor R4, comparator 122 and NAND gate 118. Resistor R4 is connected between voltage supply terminal V+ and ground terminal 90. Resistor R4 is a variable resistor having a center tap 124 connected to a non-inverting input of comparator 122. An inverting input of comparator 122 is connected to amplifier output 88. The output of comparator 122 is connected to NAND gate 118. NAND gate 118 generates a main waveform detector output 126.

Center tap 124 provides a main waveform threshold voltage at the non-inverting input of comparator 122. Comparator 122 compares amplitude of amplifier output 88 to the main waveform threshold voltage. The main waveform threshold voltage is set by adjusting center tab 124 of resistor R4. The threshold is adjusted to represent an expected amplitude of main waveform 104 (shown in FIG. 5) which arrives during main waveform time gate window 120. This value will vary depending upon the type of transducers used, the excitation frequency, the dimensions of the sensor, the physical properties of the material within the gap and the gain of amplifier 86. The output of comparator 122 is connected to NAND gate 118 together with main waveform enable signal 112 and transmit pulse disable signal 110 such that main waveform 104 is detected only during main waveform time gate window 120.

Self-test waveform detector/comparator block 74 is connected between amplifier 86 and self-test waveform integrator block 78. Block 74 includes resistor R5, comparator 128 and NAND gate 114. Resistor R5 is connected between voltage supply terminal V+ and ground terminal 90. Resistor R5 is a variable resistor having a center tap 130 which is connected to a non-inverting input of comparator 128. Amplifier output 88 is connected to an inverting input of comparator 128. The output of comparator 128 is connected to NAND gate 114. NAND gate 114 generates a self-test waveform detector output 132.

Resistor R5 generates a self-test waveform threshold voltage at center tap 130. The self-test threshold voltage is adjusted by adjusting center tap 130 to represent an expected amplitude of self-test waveform 102 within self-test waveform time gate window 116. Comparator 128 compares the amplitude of amplifier output 88 with the self-test threshold voltage. The output of comparator 128 is connected to NAND gate 114 together with self-test waveform enable signal 108 and transmit pulse disable signal 110 such that self-test waveform 102 is detected only during self-test time gate window 116.

Main waveform detector output 126 and self-test waveform detector output 132 for a sensor with a short stem are illustrated in FIG. 6. FIG. 6 is a graphical representation of the amplitude of detector waveforms 126 and 132 as a function of time. With a longer stem, the self-test waveform can come after the main waveform. The main waveform detector output 126 includes a series of pulses 134 which correspond to main waveform 104 (shown in FIG. 5) and includes a series of pulses 136 which correspond to echo waveform 106. Self-test waveform detector output 132 includes a series of pulses 138 which correspond to self-test waveform 102 (shown in FIG. 5). The presence of pulses 134 in main waveform detector output 132 indicates that main waveform 104 was present within main waveform time gate window 120. Similarly, the presence of pulses 138 in self-test waveform detector output 132 indicates that self-test waveform 102 was present within self-test waveform time gate window 116.

The main waveform detector output 126 is integrated by main waveform integrator block 76. The self-test waveform detector output 132 is integrated by self-test waveform integrator block 78. Block 76 includes inverter I5, main waveform counter and hold circuit 140 and main waveform relay driver 142. Inverter I5 is connected between NAND gate 118 and main waveform counter and hold circuit 140. Main waveform counter and hold circuit 140 is connected between inverter I5 and main waveform relay driver 142. Main waveform counter and hold circuit 140 counts the number of pulses received from NAND gate 118 during each cycle of the oscillator in transmitter 30. When the number of counted pulses exceeds a given number (such as 3) during one cycle of the oscillation, the counter generates a signal at output 146 which indicates main waveform 104 was present during main waveform time gate window 120.

Signal 146 is applied to main waveform relay driver 142 which generates main waveform output signal 80. Main waveform counter and hold circuit 140 includes a reset input 148 which is connected to transmitter 30. At the beginning of each transmit cycle of transmitter 30, transmitter 30 supplies a reset pulse which resets main counter and hold circuit 140. By counting the number of pulses during a given cycle, circuit 140 helps to eliminate false detection of main waveform 104.

As mentioned, the second set of pulses 136 shown in FIG. 6 represents echo waveforms 106 (shown in FIG. 5) within the sensor gap. The main waveform threshold voltage can be adjusted so that echo waveforms 106 in amplifier output 88 will not generate pulses on output 126 for main waveform counter and hold circuit 140. However, this is not necessary because the counter will hold its state after detecting the given number of pulses until it has been reset.

Similarly, self-test waveform detector output 132 is integrated by self-test waveform integrator block 78. Block 78 includes inverter I6, self-test waveform counter and hold circuit 150 and self-test waveform relay driver 152. Inverter I6 is connected between NAND gate 114 and self-test waveform counter and hold circuit 150. Circuit 150 is connected between inverter I6 and self-test waveform relay driver 152. Self-test waveform counter and hold circuit 150 counts the number of pulses received from self-test waveform detector output 132 during a transmit cycle. When the number of counted pulses exceeds a given value (such as 3), circuit 150 sends an output signal 154 to self-test waveform relay driver circuit 152. Self-test waveform relay driver 152 generates self-test waveform output 82 which is representative of the presence or absence of self-test waveform 102 within self-test waveform time gate window 116. Self-test waveform counter and hold circuit 150 includes a reset input 156 which is connected to transmitter 30. Circuit 150 is reset by the reset pulse from transmitter 30 at the beginning of each transmit cycle.

Main waveform output signal 80 is representative of the presence or absence of a liquid within gap 20 of sensor 10. The time gate ultrasonic sensor of the present invention can be used to sense when a liquid in a tank rises to a specified level. Sensor 10 is positioned at the specified level. When the liquid rises and enters gap 20, the velocity at which the ultrasonic signals travel through the gap increases such that the main waveform arrives at receive transducer I6 within main waveform time gate window 120. Main waveform output signal 80 will indicate that the liquid is present within gap 20.

The time gate configuration can measure density and level simultaneously because the time it takes the ultrasonic signals to travel through a material is related to the density of the material. The density measurement is made by measuring transmission time to reflect material density based on signal velocity through the material. Typically, AGC (Automatic Gain Control) is used to control main waveform amplitude when density is measured. The sensor can detect an interface between two materials in the gap based on change of signal velocity if the density of the two materials is known.

Self-test output 82 is representative of the integrity of sensor 10. If sensor 10 is functional, the self-test waveform which passes through sensor stem 18 should always be present with each transmitted pulse. This has a number of benefits. Continuous self-test can be performed even with process material in the gap and without adding piggyback crystals to test each transducer individually. The overall size of sensor 10 can therefore be reduced to accommodate a wider variety of applications.

Further, this configuration tests the complete functionality of the sensor, rather than the sensors individually. The sensor body can be constructed with a thicker stem for greater mechanical integrity. There is no need to limit the signal strength within the stem as in oscillator-type sensors of the prior art. If the signal transmitted through the stem has a higher amplitude it will improve rather than impair performance.

Sensing points can be placed closer together in multi point sensors because there is no crosstalk between each sensor. The amplitudes of the ultrasonic signals drop to an insignificant level within about one millisecond. A larger number of sensing points is permissible because less wires are required per point, and the stem can be made mechanically stronger. Less wires are required because the self-test piggyback crystals are no longer required.

The same performance can be achieved using only one transducer. In this embodiment, the measured ultrasonic signals are reflections from a surface at the other end of the gap from the transducer. For example, FIG. 7 is a sectional view of a single transducer sensor in accordance with the present invention. Sensor 160 includes body 162, bridge 164, reflector 166, transducer 168 and gap 170. Transducer 168 transmits incident waves 172 through gap 170 toward reflector 166. Reflected waves 174 return from reflector 166 through gap 170 to transducer 168. Reflector 166 is constructed so that its surface adjacent gap 170 focuses reflected waves 174 back toward crystal 168. In the embodiment shown in FIG. 7, the surface is a machined concave surface of the correct curvature for focusing the reflected waves 174 back toward crystal 168. However, reflector 166 can have a generally flat surface.

The embodiment shown in FIG. 2 can also be configured with a single transmitter which transmits and receives the ultrasonic signals. In this embodiment, main waveform 48 travels from transducer 40 along interior diameter 46 and reflects back toward transducer 40 from wall 43. Self-test waveforms 50 travel entirely around the pipe or vessel 44 along wall 43 and return to transducer 40.

The time gate configuration of the present invention can also be used to discriminate receipt of the main waveform from noise waveforms generated in the sensor stem (or supporting wall). If the signals generated in the sensor stem are not used for the self-test function, the signals in the stem are noise waveforms. The noise waveforms are generally referred to as crosstalk between the transmit transducer and the receive transducer. The main waveform enable signal allows detection of the main waveform only during the main waveform time gate window when the amplitude of the noise waveforms is significantly smaller than the amplitude of the main waveform. This provides a wide margin in which to set the main waveform threshold voltage to reject the noise waveforms. The noise waveforms therefore do not interfere with the main waveform.

The time gate ultrasonic sensor of the present invention can be used in virtually any application to measure physical properties of material within a defined space. Although the present invention has been described with reference to preferred embodiments, workers skilled in the art will recognize that changes may be made in form and detail without departing from the spirit and scope of the invention. For example, the comparisons between amplifier output 88 (shown in FIG. 4) and the threshold voltage can be done with a microprocessor that establishes the time gate windows. A software program for computer control can also be used to provide the same comparisons. DSP (Digital Signal Processing) integrated circuits can also be used to replace the circuitry shown. The stem can also be machined to include discontinuities to attenuate the self-test signal if its amplitude is too large and causes interference during the main time window. The discontinuities can be formed as ribs around the stem separated by circular grooves which can be rectangular, rounded off or triangular. The ribs act as resonant elements and soak up the signal traveling along the stem. The discontinuity thicknesses are preferably spaced a quarter wavelength apart and extend away from the stem about a half wavelength. Different dimensions can be used on different ribs on the same stem to cover a band of wavelengths. The stem, rather than being placed at the side of the sensor, can also be placed along the center axis of the sensor.

What is claimed is:

1. An automatically self-testing method of sensing whether a material is present within a defined space, the method comprising:

providing an ultrasonic sensor having transducer means connected to a support structure generally adjacent the defined space;

pulsing the transducer means to generate ultrasonic signals having a main waveform within the defined space;

providing, in response to pulsing the transducer means, a plurality of signals which define a main time window and a self-test time window which are separated in time following the pulsing of the transducer means;

receiving the ultrasonic signals with the transducer means after the signals have traveled in a first path through the defined space to form a main waveform and in a second, different self-test path to form a self-test waveform;

monitoring the received ultrasonic signals with the self-test time window to sense whether the self-test waveform is present within the self-test time window;

providing a self-test waveform output representative of proper functioning of the method if the self-test waveform is present within the self-test time window;

monitoring the received ultrasonic signals within the main time window to sense whether the main waveform is present within the main time window; and providing a main waveform output representative of the presence of the material in the defined space as a function of the presence of the main waveform within the main time window.

2. The method of claim 1 wherein the step of providing an ultrasonic sensor comprises providing the transducer means with a transmit transducer and a receive transducer which are separated by the defined space and connected by the support structure.

3. The method of claim 1 wherein the step of providing an ultrasonic sensor comprises:

providing the transducer means with a transducer which transmits and receives the ultrasonic signals; and providing the support structure with an ultrasonic reflective surface positioned across the defined space from the transducer such that the ultrasonic signals travel from the transducer to the reflective surface and then back to the transducer.

4. The method of claim 1 wherein the plurality of signals includes:

a main waveform enable signal which becomes active at a first preselected time period following pulsing the transducer means and remains active during the main time window;

a self-test waveform signal which is active following pulsing the transducer during the self-test time window;

a transmit disable signal which remains inactive following pulsing the transducer means for a second preselected time period to prevent detection of an initial transmit pulse waveform generated by the transducer means prior to the main waveform and self-test waveforms;

wherein the main waveform time window is defined by the main waveform enable signal and the transmit disable signal; and wherein the self-test waveform time window is defined by the self-test enable signal and the transmit disable signal.

5. The method of claim 4 wherein the step of monitoring the received ultrasonic signals during the main waveform time window comprises:

providing a main waveform threshold level;

comparing the amplitude of the received ultrasonic signals to the main waveform threshold level;

generating a comparison output representative of the comparison;

applying the comparison output to a main waveform integrator during the main time window; and blocking the comparison output signal from reaching the integrator outside the main time window.

6. The method of claim 5 wherein the step of providing the main waveform output representative of the presence of the material comprises:

integrating the comparison output with the integrator to sense whether the main waveform is present; and generating an output representative of the presence of the main waveform.

7. The method of claim 6 wherein the step of generating a comparison output comprises generating pulses when the received ultrasonic signals exceed the threshold level and wherein the step of integrating comprises:

counting a number of pulses in the comparison output within the main time window; and generating the output representative of the presence of the main waveform as a function of the number of pulses counted.

8. An ultrasonic sensor for detecting presence of a liquid within a defined gap, the sensor comprising:

a support structure;

a transmit signal source configured for generating a transmit signal;

transducer means, connected to the support structure and to the transmit signal source, the transducer means positioned adjacent the gap for transmitting ultrasonic signals in response to the transmit signal (a) across the gap and through the liquid if the liquid is present within the gap to define a main waveform and (b) through the support structure to define a self-test waveform, and for receiving the transmitted ultrasonic signals after the signals travel through the gap and through the support structure;

means for defining a self-test time window relative to the transmit signal and to an acoustic velocity of the self-test waveform through the support structure; and means for monitoring the received ultrasonic signals that define the self-test waveform during the self-test time window;

means for determining whether the self-test waveform is present within the self-test time window and for generating a self-test output indicative of sensor integrity as a function of whether the self-test waveform is present with the self-test time window;

time gate means, coupled to the transmit signal source, for receiving the transmit signal and for defining a main time window relative to the received transmit signal and to an acoustic velocity through the liquid;

means, coupled to the transducer means and to the time gate means, for monitoring the received ultrasonic signals during the main time window; and means, coupled to the means for monitoring, for determining whether the main waveform is present within the main time window and for generating a main waveform output indicative of whether the liquid is present within the gap as a function of whether the main waveform is present within the main time window.

9. The ultrasonic sensor of claim 8 wherein the transducer means comprises a transmit transducer and a receive transducer separated by the gap.

10. The ultrasonic sensor of claim 9 wherein the support structure comprises a bridge between the transmit transducer and the receive transducer.

11. The ultrasonic sensor of claim 8 wherein the support structure comprises a vessel having walls with a circumference and an interior diameter which defines the gap, with the transducer means connected to the vessel walls such that the ultrasonic signals travel from the transmit transducer to the receive transducer in a first path across the gap and in a second path along the circumference of the vessel walls.

12. The ultrasonic sensor of claim 8 wherein the transducer means comprises a transducer which both transmits and receives the ultrasonic signals.

13. The ultrasonic sensor of claim 8 wherein the support structure comprises an ultrasonic reflective surface positioned across the gap opposite the transducer means such that the ultrasonic signals travel in a first path from the transducer means, across the gap to the reflective surface and then back to the transducer means.

14. The ultrasonic sensor of claim 13 wherein the reflective surface comprises a concave surface with a curvature selected to focus the reflected ultrasonic signals across the gap toward the transducer means.

15. The ultrasonic sensor of claim 13 wherein the support structure further comprises a bridge which connects the transducer and the reflective surface such that the ultrasonic signals travel in a second path from the transducer means through the bridge and reflect back through the bridge to the transducer means.

16. The ultrasonic sensor of claim 8 wherein the support structure comprises a vessel having walls with a circumference and an interior diameter which defines the gap, with the transducer means being connected to the wall such that the ultrasonic signals travel in a first path from the transducer means across the interior diameter to a surface on the wall opposite the transducer means and reflect back to the transducer means and travel in a second path from the transducer means around the circumference of the wall and then back to the transducer means.

17. The ultrasonic sensor of claim 8 wherein: - the transmit signal source includes an oscillator connected to the transducer means and to the time gate means, which periodically generates the transmit signal.

18. The ultrasonic sensor of claim 8 wherein the means for monitoring comprises:

a threshold generator which generates a main waveform threshold level;

a comparator connected to the threshold generator and the received ultrasonic signals to produce a comparison output representative of a comparison of the amplitude of the received ultrasonic signals with the main waveform threshold level, the comparison output producing a pulse for each time the amplitude of the received ultrasonic signals exceeds the main waveform threshold level; and means for gating the comparison output to provide a gated pulse for each pulse produced on the comparison output during the main time window and to reject each pulse produced on the comparison output outside the main time window.

19. The ultrasonic sensor of claim 18 wherein the means for determining whether the main waveform is present within the main time window includes:

a counter, which is connected to the means for gating, for counting a number of the gated pulses provided during the main time window and for generating the output indicative of whether the main waveform is present during the main time window as a function of the number of gated pulses counted, wherein the counter includes a reset input connected to the transmit signal source for resetting the number of gated pulses counted upon receipt of the transmit signal.

20. The ultrasonic sensor of claim 18 wherein the time gate means generates a normally inactive main waveform enable signal which becomes active after a first preselected time period following receipt of the transmit signal and remains active during the main time window, wherein the main waveform enable signal enables the means for gating when active to provide the gated pulses and disables the means for gating when inactive.

21. The ultrasonic sensor of claim 20 wherein the time gate means comprises a first RC network which generates the main waveform enable signal as a function of a first RC time constant.

22. The ultrasonic sensor of claim 18 wherein:

the transducer means transmits ultrasonic signals which define an initial waveform in response to the transmit signal before transmitting the ultrasonic signals which define the main waveform; and the time gate means generates an initial waveform disable signal which is inactive for a second preselected time period to disable the means for gating and thereby reject each pulse produced by the comparison output in response to the received ultrasonic signals which define the initial waveform.

23. The ultrasonic sensor of claim 22 wherein the time gate means comprises a second RC network which generates the initial waveform disable signal as a function of a second RC time constant.

24. The ultrasonic sensor of claim 8 wherein the means for defining the self-test time window generates a normally inactive self-test enable signal which becomes active during the self-test time window and is applied to the means for monitoring the received ultrasonic signals that define the self-test waveform such that the self-test waveform is monitored only during the self-test time window.

25. The ultrasonic sensor of claim 24 wherein the means for defining the self-test time window comprises a third RC network which generates the self-test enable signal as a function of a third time constant.

26. The ultrasonic sensor of claim 8 wherein the means for monitoring the received ultrasonic signals that define the self-test waveform comprises:

a self-test threshold generator which generates a self-test waveform threshold level;

a comparator connected to the self-test threshold generator and the received ultrasonic signals to produce a self-test comparison output representative of a comparison of the amplitude of the received ultrasonic signals with the self-test waveform threshold level, the self-test comparison output producing a self-test pulse for each time the amplitude of the received ultrasonic signals exceeds the self-test waveform threshold level;

means for gating the self-test comparison output to provide a gated self-test pulse for each self-test pulse produced during the self-test time window and to reject each self-test pulse produced outside the self-test main time window.

27. The ultrasonic sensor of claim 26 wherein the means for determining whether the self-test waveform is present within the self-test time window includes:

a self-test counter, which is connected to the means for gating the self-test comparison output, for counting a number of the gated self-test pulses provided during the self-test time window and for generating the self-test output indicative of whether the self-test waveform is present during the self-test time window as a function of the number of gated self-test pulses counted, wherein the self-test counter includes a self-test reset input connected to the transmit signal source for resetting the number of gated self-test pulses counted upon receipt of the transmit signal.

28. A method of testing the integrity of an ultrasonic sensor having transducer means connected to a support structure generally adjacent a defined gap each time a measurement cycle is performed to detect presence of material in the defined gap, the method comprising:

pulsing the transmit transducer means to generate ultrasonic signals having a main waveform which tranels through the gap and a self-test waveform which travels through the support structure;

receiving the ultrasonic signals with the transducer means after the main and self-test waveforms have traveled through the gap and the support structure, respectively;

monitoring the received waveforms during a predetermined self-test time window to detect the presence of the self-test waveform within the time window;

providing a self-test output representative of sensor integrity as a function of the presence of the self-test waveform within the self-test time window;

monitoring the received waveforms during a predetermined main waveform time window which occurs after the self-test time window; and providing a main waveform output representative of presence of material in the defined gap if the main waveform is present within the main waveform time window.

29. The method of claim 28 wherein the step of monitoring the received ultrasonic signals for the self-test waveform comprises:

applying the received ultrasonic signals to a self-test waveform detector;

generating the self-test time window with a self-test waveform enable signal which becomes active at a first preselected time period following pulsing the transmit transducer and remains active during the self-test time window; and applying the self-test waveform enable signal to the self-test waveform detector to enable detection of the self-test waveform during the self-test time window.

30. The method of claim 29 wherein the step of monitoring the received ultrasonic signals further comprises:

generating the self-test time window with a transmit disable signal which remains inactive following pulsing the transducer means for a second preselected time period to prevent detection of an initial waveform generated by the transducer means prior to the main waveform; and applying the transmit disable signal to the self-test waveform detector to disable the detector when the transmit disable signal is inactive.

31. The method of claim 29 wherein the step of monitoring the received ultrasonic signals further comprises:

providing a self-test waveform threshold level;

comparing the amplitude of the received ultrasonic signals to the self-test waveform threshold level;

generating a comparison output representative of the comparison;

applying the comparison output to an integrator during the self-test time window when the self-test waveform enable signal is active; and blocking the comparison output signal from reaching the integrator outside the self-test time window when the self-test waveform enable signal is inactive.

32. The method of claim 31 wherein the step of providing a self-test output representative of sensor integrity comprises:

integrating the comparison output with the integrator to sense whether the self-test waveform is present; and generating an output representative of the presence of the self-test waveform.

33. The method of claim 32 wherein the step of generating a comparison output comprises generating pulses when the received ultrasonic signals exceed the self-test waveform threshold level and wherein the step of integrating comprises:

counting a number of pulses in the comparison output during the self-test time window; and generating the output representative of the presence of the self-test waveform as a function of the number of pulses counted.

* * * * *

UNITED STATES PATENT AND TRADEMARK OFFICE
CERTIFICATE OF CORRECTION

PATENT NO. : 5,269,188
DATED : December 14, 1993
INVENTOR(S) : Alexander J. Esin et al.

It is certified that error appears in the above-indentified patent and that said Letters Patent is hereby corrected as shown below:

On the title page:

"Attorney, Agent, or Firm", delete "Chaplin" and insert --Champlin--.

Col. 14, Line 1, delete "with" and insert --within--
(Claim 8, Line 28)

Col. 14, Line 24, "Claim 8" should be --Claim 9--
(Claim 11, LIne 1)

Col. 16, Line 42, "tranels" should be --travels--
(Claim 28, Line 8)

Signed and Sealed this

Fourth Day of October, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,269,188
DATED : December 14, 1993
INVENTOR(S) : Alexander J. Esin and Boris S. Rosselson It is certified that error appears in the above-indentified patent and that said Letters Patent is hereby corrected as shown below:

On title page,

Under [73] Assignee:

change "Rosemount Inc." to read --Kay-Ray/Sensall, Inc.--

Signed and Sealed this

Twenty-fourth Day of February, 1998

Attest:

BRUCE LEHMAN

*Attesting Officer*      *Commissioner of Patents and Trademarks*